U S010314493B2

United States Patent
Vermeulen

(10) Patent No.: US 10,314,493 B2
(45) Date of Patent: Jun. 11, 2019

(54) APPARATUS AND METHOD FOR PLAQUE DETECTION

(71) Applicant: KONINKLIJKE PHILIPS N.V., Eindhoven (NL)

(72) Inventor: Olaf Thomas Johan Antonie Vermeulen, Oss (NL)

(73) Assignee: KONINKLIJKE PHILIPS N.V., Einhdoven (NL)

( * ) Notice: Subject to any disclaimer, the term of this patent is extended or adjusted under 35 U.S.C. 154(b) by 121 days.

(21) Appl. No.: 15/513,405

(22) PCT Filed: Sep. 11, 2015

(86) PCT No.: PCT/IB2015/056975
§ 371 (c)(1),
(2) Date: Mar. 22, 2017

(87) PCT Pub. No.: WO2016/051300
PCT Pub. Date: Apr. 7, 2016

(65) Prior Publication Data
US 2017/0303791 A1    Oct. 26, 2017

Related U.S. Application Data

(60) Provisional application No. 62/056,797, filed on Sep. 29, 2014.

(51) Int. Cl.
*A61B 5/00* (2006.01)
*A46B 9/04* (2006.01)
(Continued)

(52) U.S. Cl.
CPC .............. *A61B 5/0088* (2013.01); *A46B 9/04* (2013.01); *A46B 13/02* (2013.01); *A46B 15/004* (2013.01);
(Continued)

(58) Field of Classification Search
CPC ....... A46B 9/04; A46B 13/02; A46B 15/0036; A46B 15/004; A46B 15/0044;
(Continued)

(56) References Cited

U.S. PATENT DOCUMENTS

2005/0100866 A1* 5/2005 Arnone ............... A61B 5/0088
433/215
2007/0009234 A1* 1/2007 Van De Sluis ... G06F 17/30244
386/230
(Continued)

FOREIGN PATENT DOCUMENTS

WO    2014097045 A1    6/2014
WO    2014097198 A1    6/2014

*Primary Examiner* — Nicholas D Lucchesi

(57) ABSTRACT

A plaque detection apparatus (70) and method make use of an excitation source (72), a light detector (74) and a controller (76). The excitation source (72) outputs wavelength modulated light ($\lambda_{ex}$) to an evaluation site (80) that has a periodically changing wavelength centered around a wavelength corresponding to a non-linearity in an absorption and/or a fluorescence excitation spectrum for a chosen plaque. The chosen plaque exhibits spectral characteristics different from non-chosen plaque and/or interfering species. The light detector (74) detects light ($\lambda_{site}$) (84) received from the evaluation site (80), including site reflected light ($\lambda_{refl}$) and/or site emitted light ($\lambda_{em}$). The controller (76) operatively couples to the excitation source (72) and the light detector (74) for controlling the excitation source to output the wavelength modulated light and detecting plaque as a function of the detected light ($\lambda_{site}$) and at least one higher harmonic of the wavelength modulation frequency.

7 Claims, 12 Drawing Sheets

(51) Int. Cl.
*A46B 13/02* (2006.01)
*A46B 15/00* (2006.01)

(52) U.S. Cl.
CPC ...... *A46B 15/0036* (2013.01); *A46B 15/0044* (2013.01); *A46B 15/0046* (2013.01); *A61B 5/0071* (2013.01); *A61B 5/0075* (2013.01); *A61B 5/4547* (2013.01); *A46B 2200/1066* (2013.01)

(58) Field of Classification Search
CPC . A46B 15/0046; A61B 5/0071; A61B 5/0075; A61B 5/4547; A61B 2200/1066
See application file for complete search history.

(56) References Cited

U.S. PATENT DOCUMENTS

| | | | |
|---|---|---|---|
| 2007/0021670 A1 | 1/2007 | Mandelis et al. | |
| 2015/0286340 A1* | 10/2015 | Send | G01S 17/46 345/175 |
| 2015/0305626 A1* | 10/2015 | Deane | A61B 5/7228 433/27 |

* cited by examiner

APPARATUS AND METHOD FOR PLAQUE DETECTION

CROSS-REFERENCE TO PRIOR APPLICATIONS

This application is the U.S. National Phase application under 35 U.S.C. § 371 of International Application No. PCT/IB2015/056975, filed on Sep. 11, 2015, which claims the benefit of U.S. Provisional Patent Application No. 62/056,797, filed on Sep. 29, 2014. These applications are hereby incorporated by reference herein.

The present embodiments relate generally to oral healthcare apparatus and methods and more particularly, to plaque detection apparatus and method for plaque detection.

Oral healthcare is important in support of good hygiene and health of teeth. In particular, good oral healthcare includes the removal of dental plaque. Dental plaque is defined clinically as a structured, resilient, yellow greyish substance that adheres tenaciously to the intraoral hard surfaces, including removable and fixed restorations. In addition, dental plaque comprises an oral bio-film characterized by its organized structure consisting of a multitude of bacteria and fluid-filled channels. Plaque is primarily composed of bacteria in a matrix of salivary glycol-proteins and extracellular polysaccharides. Furthermore, one gram of plaque contains approximately $10^{11}$ bacteria. More than 500 distinct microbial species are found in dental plaque. Moreover, based on its position on a tooth surface, dental plaque is classified into supragingival plaque or subgingival plaque.

Oral plaque comprises a complexity of hundreds of species of bacteria. The maturation of oral plaque is very variable, depending on location in the mouth, age, time, oral environment and other factors. Despite this variability, analyses of oral plaque have shown that it develops according to reproducible patterns. The majority of cultivable bacteria in dental plaque are *Streptococcus mutans, Streptococcus sanguinis* and *Streptococcus miteor.*

With respect to Supragingival plaque, the dental plaque follows a typical growth pattern with initial growth along the gingival margin and interdental space, which further extends in a coronal direction. Rough surfaces like grooves in teeth, denture bases and crowns retain more plaque. With respect to variation within the dentition, plaque formation occurs faster in the lower jaw when compared to the upper jaw, and in molar areas. In addition, individual variables like brushing habits, smoking, diet, chemical composition of saliva and pellicle also influence plaque formation.

It would thus be desirable to help users when cleaning their teeth by informing them whether they are indeed removing plaque from their teeth and whether they have fully removed the plaque. In this manner, the users are provided with reassurance, in addition to being coached into good oral hygiene habits. Preferably, the information should be provided in real time during brushing, as otherwise consumer acceptance is likely to be low. For example, it would be useful if a toothbrush provides the user with a signal of when the position at which the user is currently brushing is free of plaque, so that the user can move on to the next brushing position of teeth to be cleaned. This may reduce the user's brushing time, as well as, also lead to a better, more conscious brushing routine.

A power toothbrush, or other oral healthcare appliance, having a capability to detect plaque in the presence of interfering species, e.g., in a vibrating brush system surrounded with toothpaste foam, would be desirable. The detection system should provide contrast between a surface with the removable plaque layers and a cleaner pellicle/calculus/dental filling/tooth surface. However, existing power toothbrushes are not known to detect the absence or presence of plaque.

Accordingly, an improved method and apparatus for overcoming the problems in the art is desired.

According to the embodiments of the present disclosure, the apparatus and method advantageously provide a way to detect plaque in real-time during a brushing routine. The apparatus and method implement plaque detection based on the shape of one or more of the absorption and fluorescence excitation spectrum of plaque. In particular, the nonlinearity of one or more of the absorption and fluorescence excitation spectrum of plaque allows for the generation of absorption and emission harmonics by changing the wavelength of a probing light source periodically. Synchronous measurement of these harmonics allows plaque detection with large suppression of background signals.

According to other embodiments, an optical probe and method for detecting dental plaque can be integrated in a toothbrush. The plaque detection method is based on the generation of harmonics due to the non-linear shape of one or more of the absorption and fluorescence excitation spectrum of plaque, and the subsequent detection of one of these harmonics. Detection takes place in the absorption spectrum (reflected light) and/or emitted spectrum (fluorescence emission).

According to one aspect, a plaque detection apparatus comprises an excitation source, a light detector, and a controller. The excitation source is configured for outputting wavelength modulated light ($\lambda_{ex}$) to an evaluation site, the wavelength modulated light being modulated at a wavelength modulation frequency to have a periodically changing wavelength centered around a wavelength corresponding to a non-linearity in one or more of an absorption and a fluorescence excitation spectrum for a chosen plaque. The chosen plaque exhibits spectral characteristics different from spectral characteristics of one or more of (i) non-chosen plaque and (ii) interfering species other than the chosen plaque. The light detector is configured for detecting light ($\lambda_{site}$) received from the evaluation site, wherein the detected light ($\lambda_{site}$) comprises one or more of (i) a site reflected light ($\lambda_{refl}$) and (ii) a site emitted light ($\lambda_{em}$). The controller is operatively coupled to the excitation source and the light detector for (i) controlling the excitation source to output the wavelength modulated light and (ii) detecting plaque as a function of the detected light ($\lambda_{site}$) and at least one higher harmonic of the wavelength modulation frequency higher than a fundamental.

According to another aspect, the controller comprises an excitation control module for controlling, via at least one excitation control signal, the excitation source to output the wavelength modulated light, and a harmonic component detection module for detecting at least one harmonic component of the wavelength modulation frequency higher than a fundamental component contained within at least one of (i) an absorption spectrum that comprises site reflected light ($\lambda_{refl}$) and (ii) an excitation spectrum that comprises fluorescence emission in site emitted light ($\lambda_{em}$). In a further aspect, the harmonic component detection module comprises at least one lock-in amplifier configured to detect the at least one higher harmonic component of the wavelength modulation frequency and to reject signals modulated at other frequencies.

According to yet another aspect, the controller outputs at least one signal as a function of detected plaque and indicative of a characteristic at the evaluation site that comprises at least one selected from the group consisting of (i) a presence of plaque, (ii) young plaque, (iii) mature plaque, and (iv) an absence of plaque. In another aspect, the periodically changing wavelength includes the use of wavelengths that comprise (i) a central wavelength that aligns with the non-linearity in the one or more of the absorption and fluorescence excitation spectrum for the chosen plaque, (ii) a wavelength shorter than the central wavelength, and (iii) a wavelength longer than the central wavelength.

According to a further aspect, the plaque detection apparatus further comprises an optics module that includes at least one of optical filters, optical fibers, collecting optical elements, and focusing optical elements optically coupled in a path of at least one of (i) the wavelength modulated light ($\lambda_{ex}$) from the excitation source to the evaluation site and (ii) the detected light ($\lambda_{site}$) from the evaluation site to the light detector.

In one embodiment, the excitation source comprises three LEDs for use in outputting three different wavelengths of light, the light detector comprises at least one photodetector, and the excitation control module includes a sequence generator for outputting the at least one excitation control signal configured for sequencing an excitation of the three LEDs to produce a resultant light output having the periodically changing wavelength centered around the wavelength corresponding to the non-linearity in the one or more of the absorption and the fluorescence excitation spectrum for the chosen plaque.

In another embodiment, the three LEDs comprise blue LEDs that each output a narrow spectrum of light, and the three different narrow spectra of light comprise 438 nm, 444 nm and 450 nm. In yet another embodiment, the three LEDs have an emission spectrum sufficient to cover a required range of the three different narrow spectra of light, wherein the excitation source further comprises three clean-up filters arranged respectively at outputs of the three LEDs, one clean-up filter per LED, wherein each of the three clean-up filters has a pass-band for a respective one of the three different narrow spectra of light.

According to another embodiment, the excitation source comprises a laser diode, wherein the light detector comprises at least one photodetector, and wherein the excitation control module outputs the at least one excitation control signal configured for exciting the laser diode to produce a resultant light output having the periodically changing wavelength centered around the wavelength corresponding to the non-linearity in the one or more of the absorption and the fluorescence excitation spectrum for the chosen plaque.

According to yet another embodiment, the light detector comprises a photodetector for use in detecting site reflected light, and one bandpass filter, wherein the bandpass filter has a pass-band for separating out a desired band of the site reflected light centered around the wavelength corresponding to the non-linearity in the absorption spectrum for the chosen plaque, while rejecting other bands of site reflected light.

According to a further embodiment, the excitation source comprises a wide emission spectrum fixed wavelength light source and a tunable filter arranged at an output of the wide emission spectrum fixed wavelength source, wherein tunable filter is operable for modulating a pass-band of the tunable filter among different wavelengths, wherein the light detector comprises at least one photodetector, and wherein the excitation control module outputs the at least one excitation control signal configured for tuning the tunable filter to produce a resultant light output having the periodically changing wavelength centered around the wavelength corresponding to the non-linearity in the one or more of the absorption and the fluorescence excitation spectrum for the chosen plaque.

In a still further embodiment, the excitation source comprises a wavelength tunable light source, wherein wavelength tunable light source is operable for being modulated among different wavelengths, wherein the light detector comprises at least one photodetector, and wherein the excitation control module outputs the at least one excitation control signal configured for tuning the wavelength tunable light source to produce a resultant light output having the periodically changing wavelength centered around the wavelength corresponding to the non-linearity in the one or more of the absorption and the fluorescence excitation spectrum for the chosen plaque.

According to another aspect, an oral healthcare appliance includes the plaque detection apparatus according to embodiments herein. The oral healthcare appliance further comprises a handle portion for housing at least a first portion of the plaque detection apparatus, and a distal end portion, extending from the handle portion and being optically coupled via an optics module with the plaque detection apparatus, for evaluating a site for a presence of plaque via the distal end portion, the distal end portion comprising at least one of (i) toothbrush bristles, and (iii) a probe absent a presence of toothbrush bristles, and wherein the optics module includes at least one of optical filters, optical fibers, collecting optical elements, and focusing optical elements optically coupled in a path of at least one of (i) the wavelength modulated light ($\lambda_{ex}$) from the excitation source to the evaluation site and (ii) the detected light ($\lambda_{site}$) from the evaluation site to the light detector.

According to a further aspect, a plaque detection method, comprises: providing wavelength modulated light ($\lambda_{ex}$) to an evaluation site, the wavelength modulated light being modulated at a wavelength modulation frequency to have a periodically changing wavelength centered around a wavelength corresponding to a non-linearity in one or more of an absorption and a fluorescence excitation spectrum for a chosen plaque, wherein the chosen plaque exhibits spectral characteristics different from spectral characteristics of one or more of (i) other plaque and (ii) interfering species other than the chosen plaque; detecting light ($\lambda_{site}$) received from the evaluation site, wherein the detected light ($\lambda_{site}$) comprises one or more of (i) a site reflected light ($\lambda_{refl}$) and (ii) a site emitted light ($\lambda_{em}$); and detecting plaque as a function of the detected light ($\lambda_{site}$) and at least one higher harmonic component of the wavelength modulation frequency higher than a fundamental.

Still further advantages and benefits will become apparent to those of ordinary skill in the art upon reading and understanding the following detailed description.

The embodiments of the present disclosure may take form in various components and arrangements of components, and in various steps and arrangements of steps. Accordingly, the drawings are for purposes of illustrating the various embodiments and are not to be construed as limiting the embodiments. In the drawing figures, like reference numerals refer to like elements. In addition, it is to be noted that the figures may not be drawn to scale.

Figure 14:
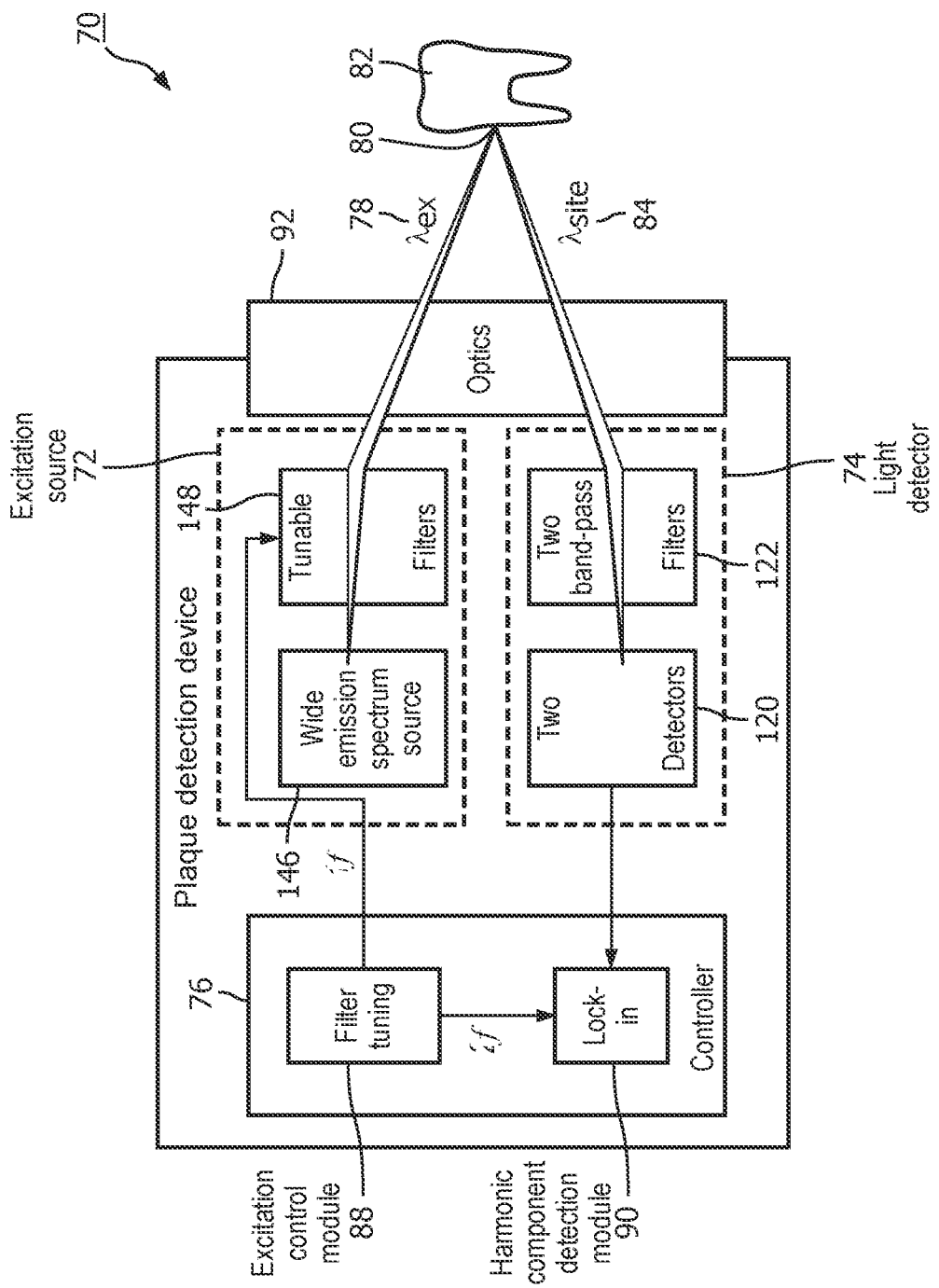
Figure 15:
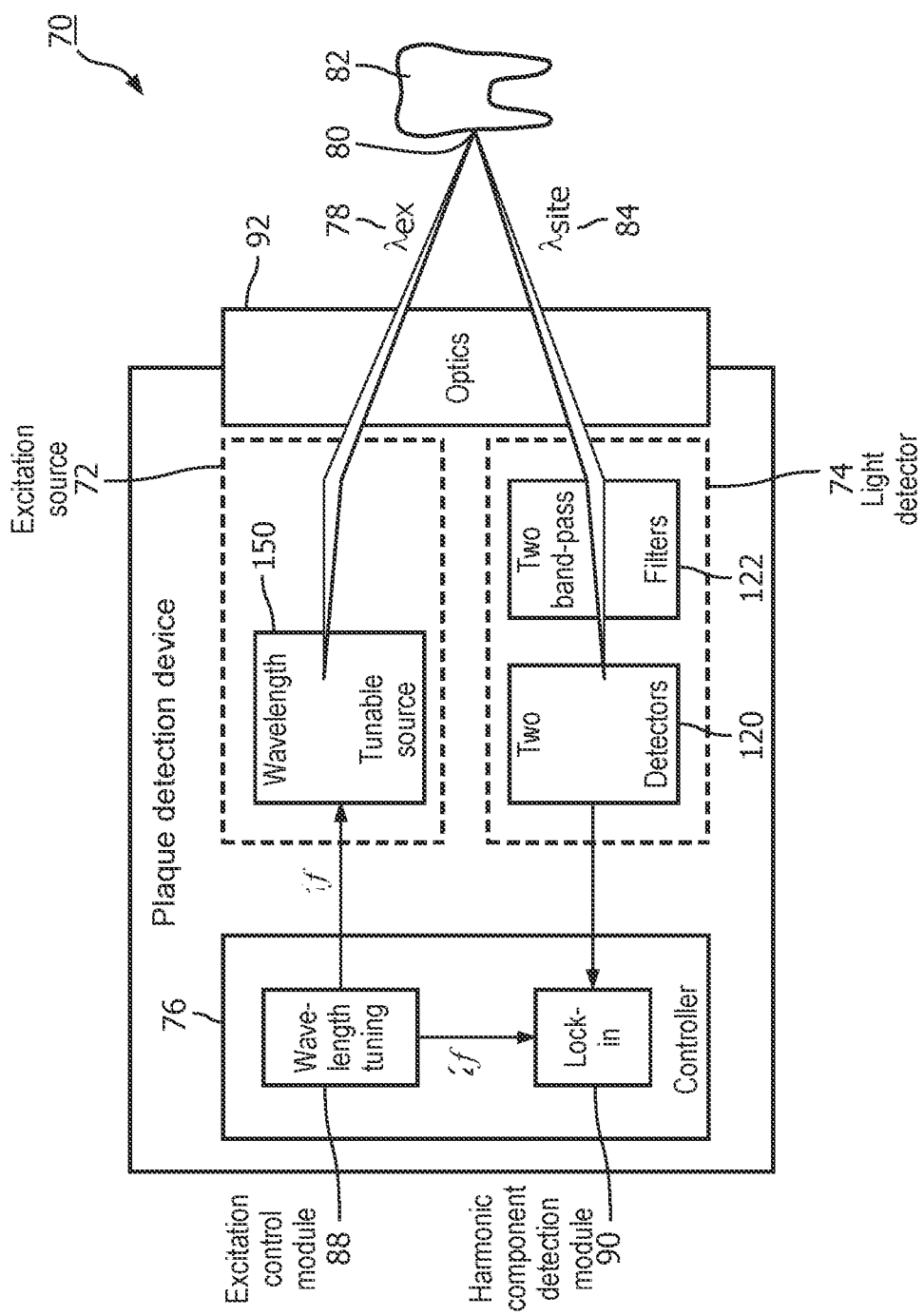

FIG. 14 is a block diagram view of a plaque detection apparatus that includes an excitation source having a wide emission spectrum source and tunable filter, for detecting plaque using evaluation site emitted and/or reflected light, according to an embodiment of the present disclosure; and FIG. 15 is a block diagram view of a plaque detection apparatus that includes an excitation source having a wavelength tunable source, for detecting plaque using evaluation site emitted and/or reflected light, according to an embodiment of the present disclosure.

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known devices, components and/or processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein can be used in the practice or testing of the embodiments.

According to the embodiments of the present disclosure, the apparatus and method advantageously provides a way to detect plaque in real-time during a brushing routine. The apparatus and method implement plaque detection based on the shape of one or more of the absorption and fluorescence excitation spectrum of plaque. In particular, the nonlinearity of one or more of the absorption and fluorescence excitation spectrum of plaque allows for the generation of absorption and emission harmonics by changing the wavelength of a probing light source periodically. Synchronous measurement of these harmonics allows plaque detection with large suppression of background signals. As discussed herein, the plaque detection method is based on the generation of harmonics due to the non-linear shape of one or more of the absorption and fluorescence excitation spectrum of plaque, and the subsequent detection of one of these harmonics. Detection takes place in the absorption spectrum (reflected light) and/or emitted spectrum (fluorescence emission).

Autofluorescence properties of plaque are generally known and can be divided into two "colors" depending on the type of plaque: young plaque or mature plaque. Of the two, the latter is easy to detect because it shows red fluorescence when excited with blue light. However, when practicing good oral hygiene, this type of plaque should rarely be encountered. Therefore, the detection of the young plaque is of more importance. Unfortunately, young plaque shows the same fluorescence properties as dental hard tissue, i.e., green fluorescence (peaking around 500-510 nm) on blue excitation. This makes fluorescence detection of young plaque on enamel unfeasible. To make matters worse, composite dental fillings show similar fluorescence properties as young plaque. There is however a great difference in the excitation spectra of, on the one hand, plaque, and on the other, dental hard tissue and fillings.

Figure 1:
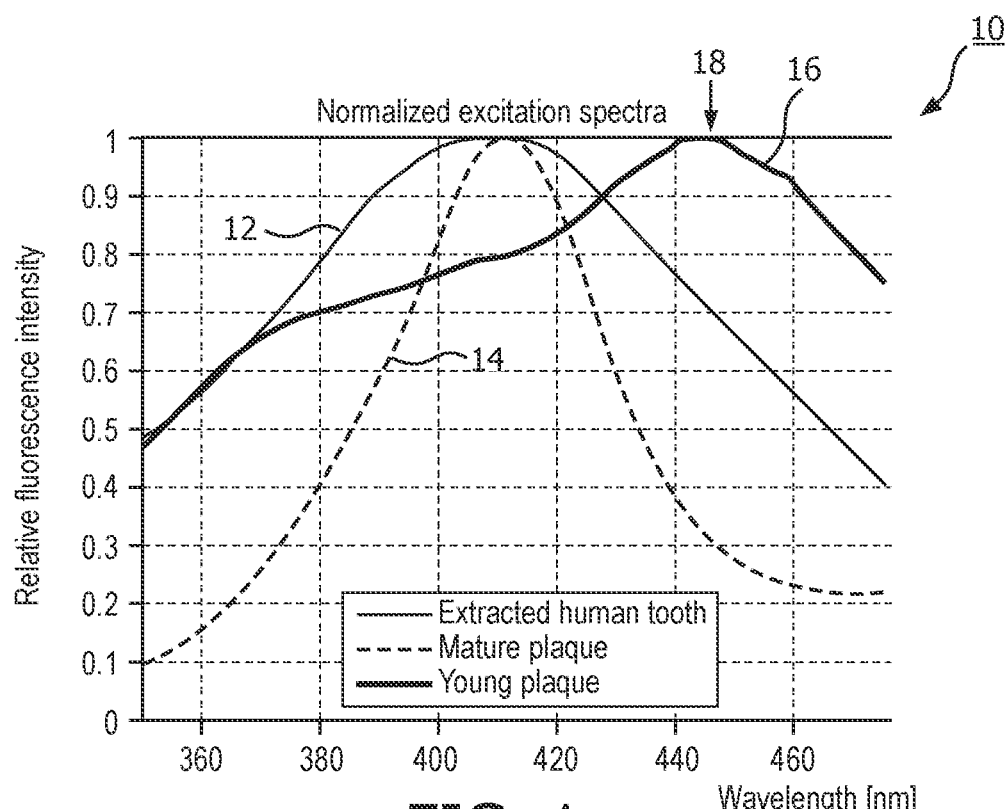
FIG. 1 is a graphical view of a normalized excitation spectra for each of an extracted human tooth and ex vivo young and mature plaque samples.

With reference now to FIG. 1, a graphical view 10 of normalized excitation spectra for each of an extracted human tooth and ex vivo young and mature plaque samples is shown. In FIG. 1, normalized relative fluorescence intensity is plotted as a function of excitation wavelength (nm). The normalized excitation spectra is identified for the tooth by reference numeral 12, for the mature plaque sample by reference numeral 14, and for the young plaque by reference numeral 16. All spectra were recorded on an Edinburgh Instruments FLSP920 time resolved fluorescence spectrometer. For the excitation and emission measurements the steady state configuration using the Xe900 continuous xenon lamp was applied. In addition, the following settings were used. Spectra were recorded with 1.1 mm slit opening of the excitation and emission monochromators giving a 1 nm excitation resolution, a 1 nm emission resolution and a 0.5×4 mm excitation spot-size. The detector used was a FLSP920 standard photomultiplier (Hamamatsu, R928P) with a spectral coverage from 200 nm to approximately 870 nm. The detector operation temperature was actively controlled to −20° C. Spectra were recorded with correction for dark current, excitation intensity and detector sensitivity.

In FIG. 1, a peak (indicated by reference numeral 18) in relative fluorescence intensity can be clearly observed around 450 nm (i.e., more closely to 444 nm) in relative fluorescence intensity of the normalized spectrum of young plaque 16. At the same wavelengths around 450 nm (e.g., 440 nm to 460 nm), there is a certain nonlinearity in the relative fluorescence intensity of the normalized spectrum of mature plaque 14, while the excitation spectrum of human teeth 12 is locally linear there.

Advantageously, the embodiments of the present disclosure make use of the non-linearity in the excitation spectra around 450 nm to detect plaque. In particular, by synchronous detection of the harmonics in the detected light, background signals like that of dental hard tissue, toothpaste, gum (gingiva) and fillings are advantageously rejected, while at the same time, plaque can be detected reliably. The embodiments of the present disclosure also advantageously allow for making a distinction between mature and young plaque. While the embodiment of the illustrative example discussed herein takes into account the non-linearity that occurs in the wavelength range around 450 nm, there are additional non-linearity ranges in the spectra which could be exploited. The example discussed herein focuses on the 450 nm area because of an availability of applicable light sources, e.g., diode lasers or LEDs. (E.g., Cree produces 450 nm LEDs in 2.5 nm wide bins ranging from 445 nm to 465 nm). Also, 450 nm is a good excitation wavelength for plaque fluorescence. However, as light sources with other wavelength ranges become available in the future, exploitation of other non-linearity ranges in the spectra can also be used.

A simulation was used to determine what would happen if each matter (i.e., dental hard tissue, young and mature plaque) was excited with light, from a light source probing a tooth site, that is linearly swept in wavelength from 440 nm to 470 nm for four periods, i.e., a sawtooth modulated wavelength. The response is the simulated fluorescence emission of FIG. 2.

Figure 2:
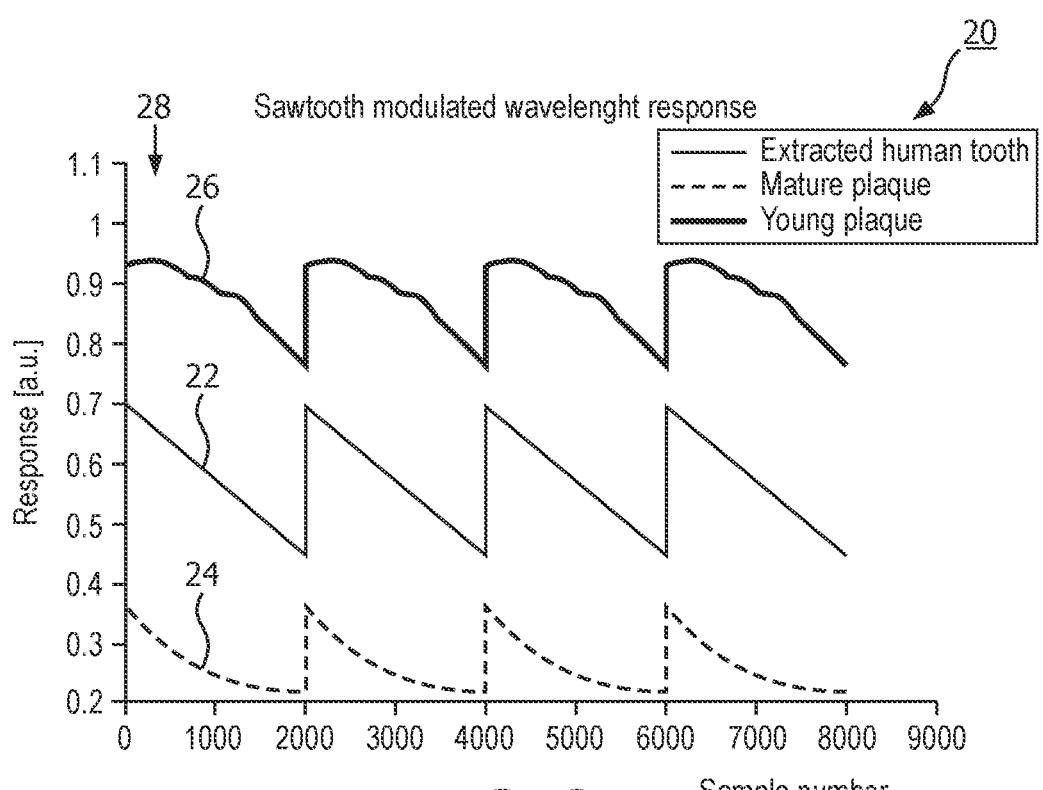
FIG. 2 is an illustrative view of a sawtooth modulated wavelength response plotted as a function of sample number of a simulated fluorescence emission for each of the extracted human tooth, and ex vivo young and mature plaque samples.

With reference now to FIG. 2, a plot, identified by reference numeral 20, of the sawtooth modulated wavelength response (expressed in arbitrary units (a.u.)) as a function of sample number of the simulated fluorescence emission for each of the extracted human tooth, and ex vivo young and mature plaque samples is shown. The sawtooth modulated wavelength responses for the extracted human tooth, the mature plaque, and the young plaque are identified via reference numerals 22, 24 and 26, respectively. It is to be noted that the individual responses 22, 24 and 26 each have been given an offset for display purposes only, so that the traces do not overlap. In addition, the sweep range is exaggerated, both for display purposes and to show the opposite effects in young and mature plaque. For example, in an interval identified by reference numeral 28 which extends over the sample numbers 0 to 2000, the modulated wavelength response for mature plaque 24 displays an upward facing curve characteristic, whereas the modulated wavelength response for young plaque 26 displays a downward facing curve characteristic. This opposite effect translates into a phase difference in the frequency spectra between both types of plaque.

With reference still to FIG. 2, it is clear that the tooth response 22 just follows the wavelength change, i.e., no distortion is visible. However, the response of both mature and young plaque, 24 and 26, respectively, clearly shows nonlinearity. This nonlinearity introduces harmonics which can be detected using synchronous detection. On the other hand, a direct frequency doubling capability of the young plaque is not yet clear from the sawtooth modulated wavelength response. This will become clear in the next figure relating to a sinewave modulated wavelength response.

Figure 3:
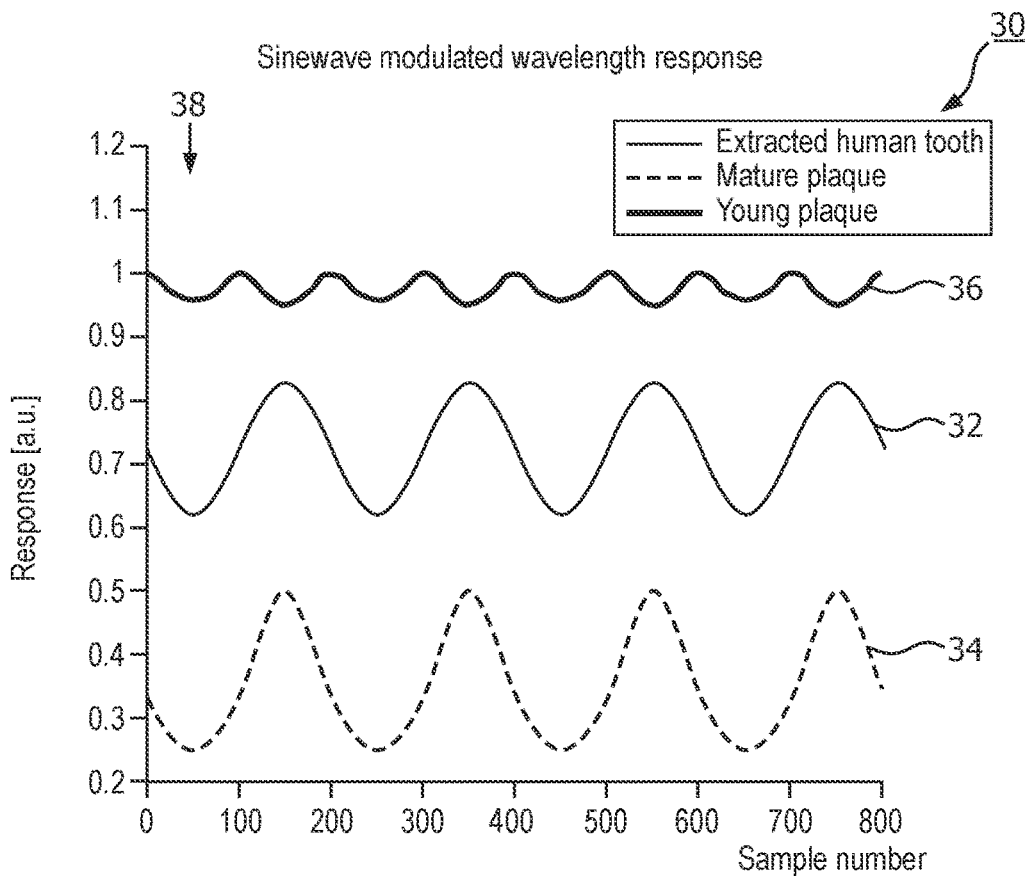
FIG. 3 is an illustrative view of a sinewave modulated wavelength response plotted as a function of sample number of a simulated fluorescence emission for each of the extracted human tooth, and ex vivo young and mature plaque samples.

With reference now to FIG. 3, a plot, identified by reference numeral 30, of a sinewave modulated wavelength response (expressed in arbitrary units (a.u.)) plotted as a function of sample number of a simulated fluorescence emission for each of the extracted human tooth, and ex vivo young and mature plaque samples is shown. The sinewave modulated wavelength responses for the extracted human tooth, the mature plaque, and the young plaque are identified via reference numerals 32, 34 and 36, respectively. It is to be noted that the individual responses 32, 34 and 36 each have been given an offset for display purposes only, so that the traces do not overlap. In addition, the sweep range is exaggerated, both for display purposes and to show the opposite effects in young and mature plaque. As illustrated, in an interval identified by reference numeral 38 which extends over the sample numbers 0 to 200, the modulated wavelength response for mature plaque 34 displays a sinusoidal characteristic and the modulated wavelength response for young plaque 36 displays a frequency doubled sinusoidal characteristic. With reference still to FIG. 3, the wavelength modulation of the excitation source light output was centered around a wavelength corresponding to a non-linearity (e.g., an emission peak) of the fluorescence excitation or emission spectrum for young plaque.

Figure 4:
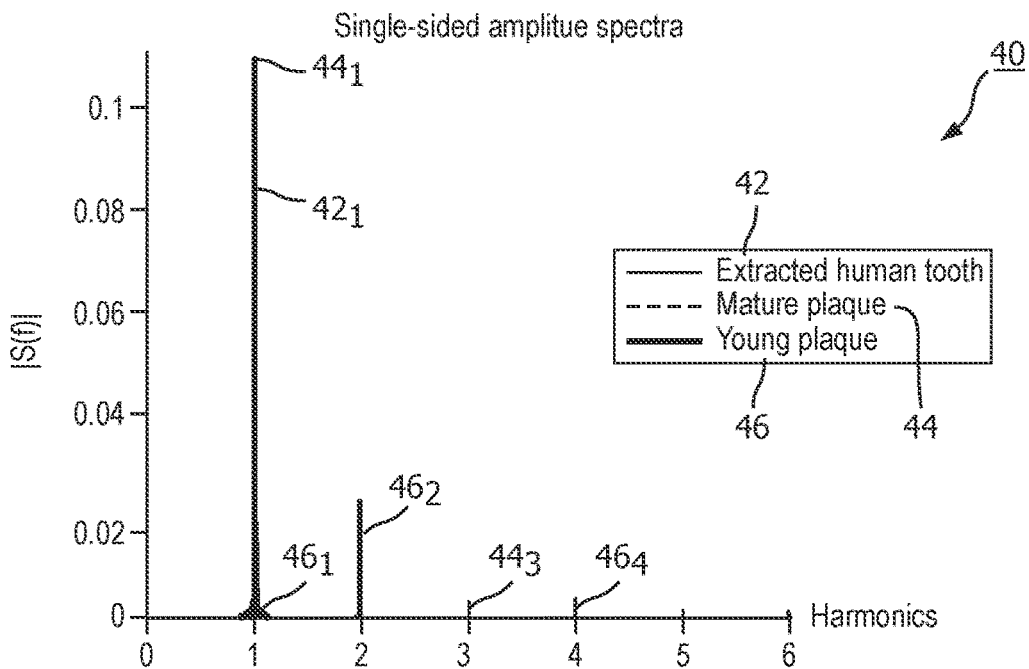
FIG. 4 is an illustrative view of a single-sided amplitude spectra of a Fast Fourier Transform (FFT) frequency analysis of the signals of FIG. 3, wherein the first harmonic identified by number 1 comprises the fundamental harmonic, according to an embodiment of the present disclosure.

Turning now to FIG. 4, there is shown an illustrative view 40 of a single-sided amplitude spectra of a Fast Fourier Transform (FFT) frequency analysis of the signals of FIG. 3. More particularly, FIG. 4 illustrates the FFT of the signals of FIG. 3, where the vertical axis |S(f)| represents a magnitude of the spectrum as a function of frequency and the horizontal axis represents harmonics. The first harmonic is identified by the number 1 and comprises the fundamental harmonic. The second harmonic is identified by the number 2, the third harmonic is identified by the number 3, and so on. The FFT results in both positive and negative frequencies; however, the single-sided amplitude spectrum essentially discards the negative frequencies while correcting for amplitude (i.e., doubling positive frequency amplitude to compensate for energy in negative frequencies). In FIG. 4, the single-sided amplitude spectra for the human tooth, mature plaque, and young plaque are identified via reference numerals 42, 44, and 46, respectively.

In the single-sided amplitude spectra 40 of FIG. 4, at the first harmonic, a magnitude of the spectral contribution resulting from the human tooth at the first harmonic is identified at $42_1$ and a magnitude of the spectral contribution resulting from the mature plaque at the first harmonic is identified at $44_1$, which is slightly greater than that of the human tooth at the first harmonic. The spectral contribution resulting from the young plaque at the first harmonic, however, is significantly less than both that of the mature plaque and the tooth, as will be discussed further with reference to FIG. 5. Referring still to FIG. 4, it is further noted that at the second harmonic, there is a magnitude of spectral contribution resulting from the young plaque identified at $46_2$, while the magnitudes of spectral contributions are less from the mature plaque and minimal from the tooth. Similarly, the third harmonic shows a contribution from mature plaque identified at $44_3$, and while not identified, the third harmonic also includes a contribution from young plaque which is less than that of the mature plaque. In a similar manner, the fourth harmonic shows a principal contribution by young plaque, identified at $46_4$. Contributions at the fifth and sixth harmonics are significantly smaller and not discernible in this view.

Figure 5:
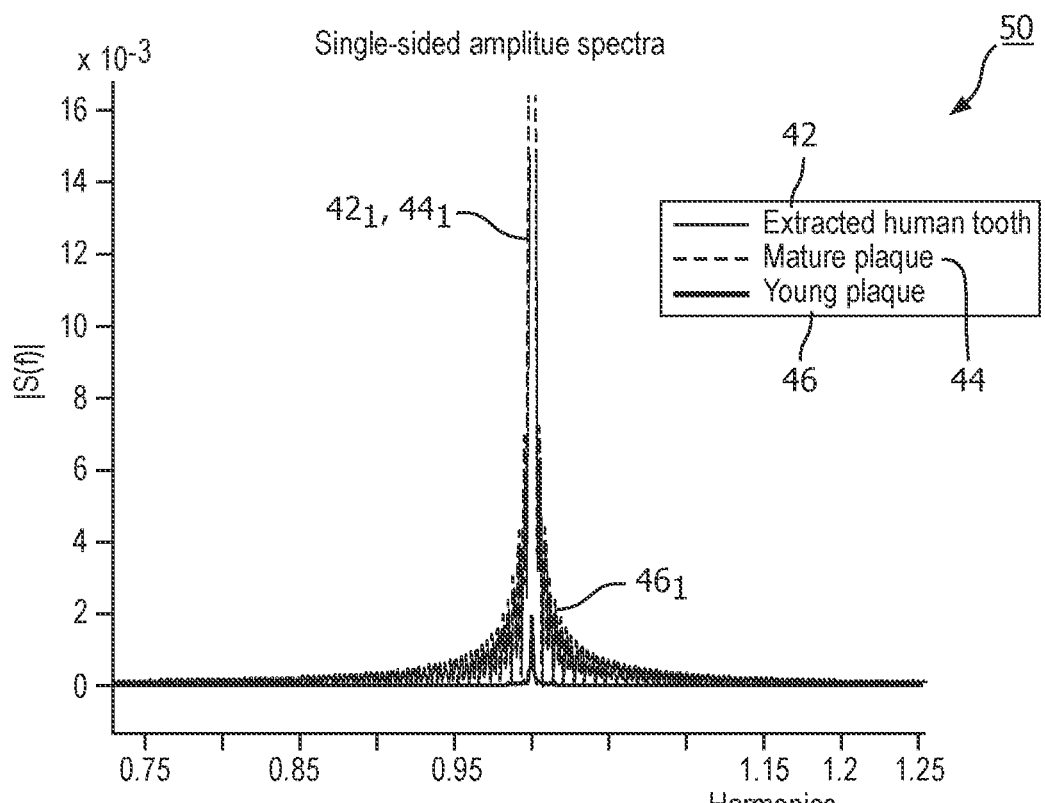
FIG. 5 is an illustrative view of a close-up of the single-sided amplitude spectra of FIG. 4, zoomed-in on the first harmonic, according to an embodiment of the present disclosure.

With reference now to FIG. 5, there is shown a close-up illustrative view 50 of the single-sided amplitude spectra of FIG. 4, zoomed-in on the first harmonic. In this view, the single-sided amplitude spectra for the human tooth, mature plaque, and young plaque are identified via reference numerals 42, 44, and 46, respectively, as in FIG. 4. As expected, no useful information is obtained from the fundamental or first harmonic 1 in the figure. In FIG. 5, the traces overlap to a certain extent, however, the fundamental component for the tooth $42_1$ and mature plaque $44_1$ are approximately equally large while the fundamental component for the young plaque $46_1$ is little to none.

Figure 6:
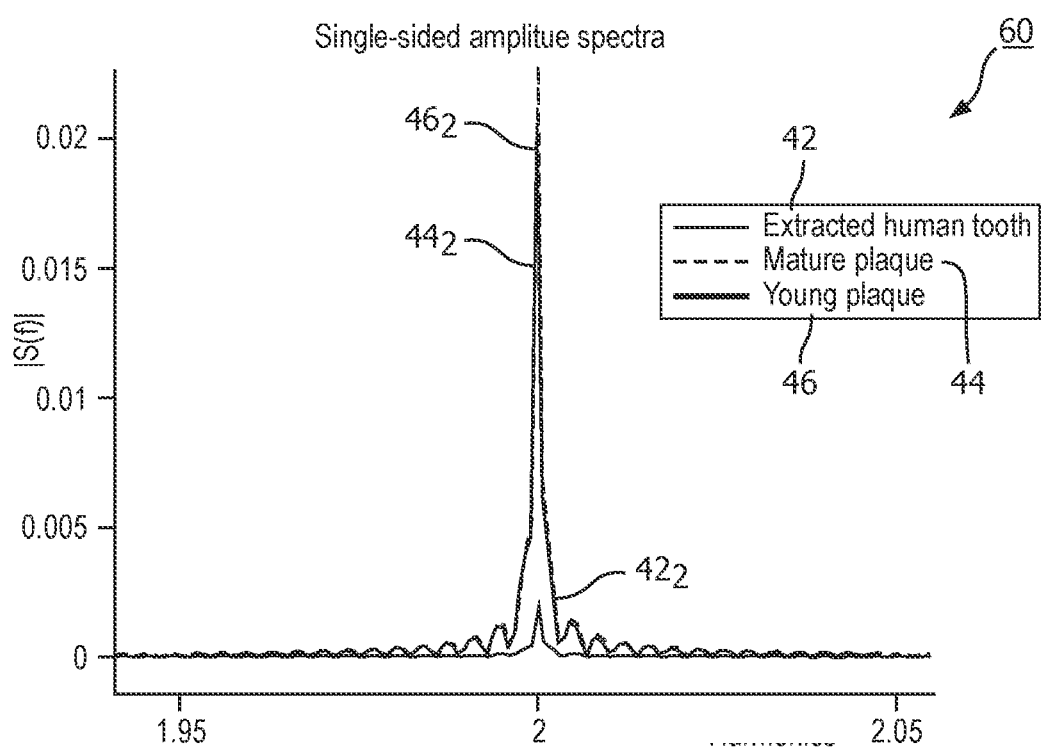
FIG. 6 is an illustrative view of a close-up of the single-sided amplitude spectra of FIG. 4, zoomed-in on the second harmonic, according to an embodiment of the present disclosure.

Turning now to FIG. 6, there is shown an illustrative view 60 of a close-up of the single-sided amplitude spectra of FIG. 4, zoomed-in on the second harmonic 2, according to an embodiment of the present disclosure. In this view, the second harmonic shows the largest contribution from young plaque $46_2$ (which is also the case for the 4 th and 6 th harmonic, illustrated in FIG. 4 via reference numbers $46_4$ and $46_6$), while the contribution from the tooth $42_2$ at the second harmonic (and higher harmonics) is at least an order of magnitude lower (e.g., possibly caused by FFT leakage). An estimation of the contribution from mature plaque at the second harmonic 2 is indicated at $44_2$, which is less than that of the young plaque $46_2$.

Synchronous measurement of the second harmonic therefore makes plaque detection independent from the tooth background signal. In addition, separation of mature and young plaque is possible from (i) the third harmonic or (ii) from the phase at the second harmonic. In one embodiment, the separation of mature and young plaque from the phase at the second harmonic might be preferable to save an additional lock-in amplifier at the third harmonic. In other words, detecting the phase at the second harmonic would eliminate the need for an additional lock-in amplifier to detect the signal at the third harmonic. Although, it should be further noted that embodiments implemented with the use of digital lock-in amplifiers would only require additional firmware to detect the third harmonic.

According to the embodiments of the present disclosure, the plaque detection signal can comprise the use of a reflected signal (i.e., absorption spectrum) and/or an emission spectrum (i.e., fluorescence). Using fluorescence, the separation between mature and young plaque is also possible through wavelength filtering.

The embodiments of the present disclosure further make use of an effect based on the generation of harmonics in the received light, caused by periodically changing the wavelength of a probing light source. In some embodiments, a light source with two or more wavelength generation means, one or more photo detector means to detect the reflected light; and one or more synchronous detection means (e.g. lock-in amplifiers) are included.

Figure 7:
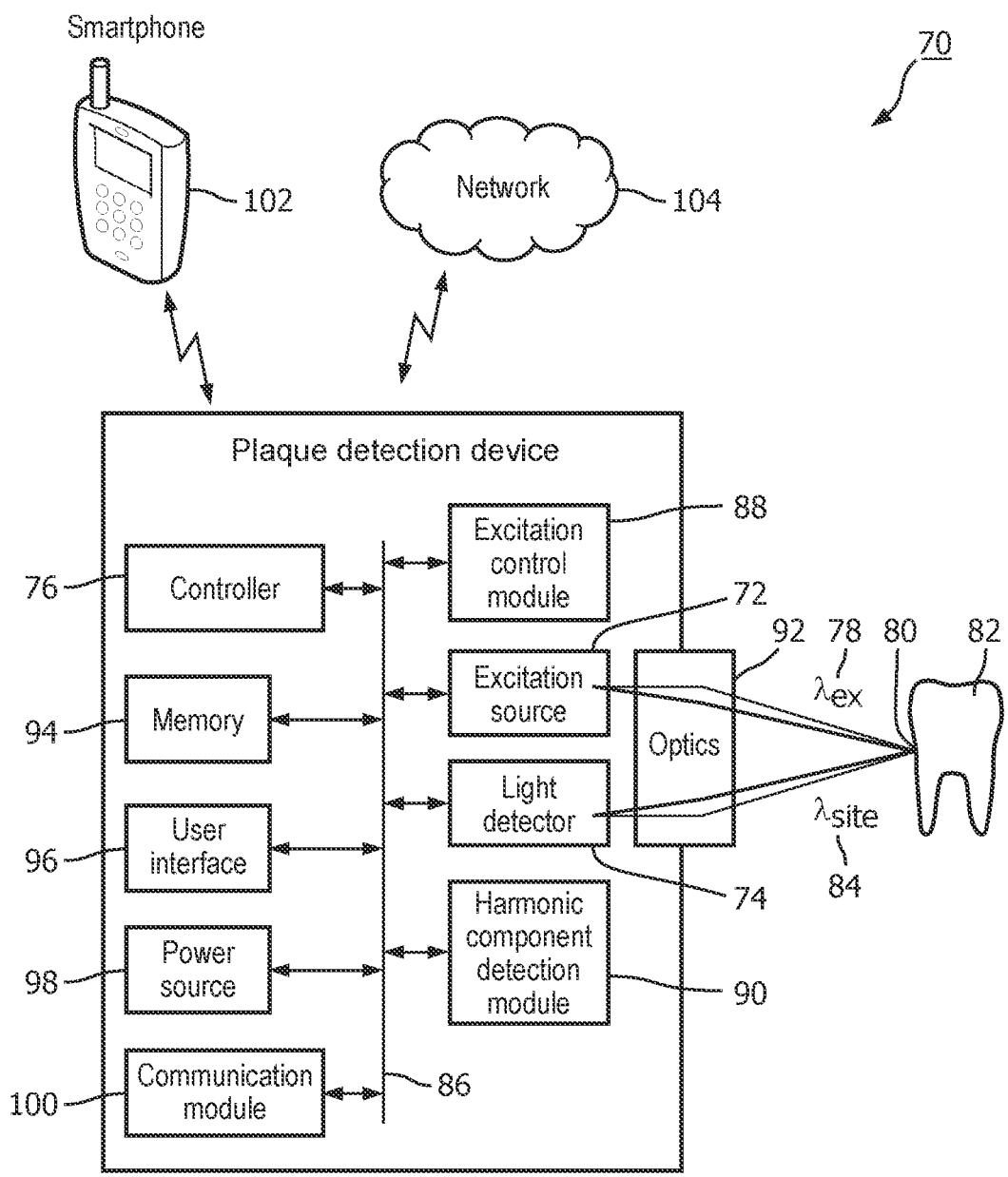
FIG. 7 is an illustrative block diagram view of a plaque detection apparatus according to an embodiment of the present disclosure.

With reference now to FIG. 7, an illustrative block diagram view of a plaque detection apparatus or device 70 according to an embodiment of the present disclosure is shown. The plaque detection device 70 comprises at least an excitation source 72, a light detector 74 and a controller 76. The excitation source 72 is configured for outputting wavelength modulated light ($\lambda_{ex}$), identified by reference numeral 78, to an evaluation site 80, for example, on a tooth 82. Additional details regarding the excitation source 72 will be provided herein below with reference to FIGS. 8 and 11-15.

In one embodiment, the output wavelength modulated light 78 of excitation source 72 is modulated at a wavelength modulation frequency to have a periodically changing wavelength centered around a wavelength corresponding to a non-linearity in one or more of an absorption and a fluorescence excitation spectrum for a chosen plaque. The chosen plaque exhibits spectral characteristics different from spectral characteristics of one or more of (i) a non-chosen plaque and (ii) interfering species other than the chosen plaque. For example, the chosen plaque can comprise young plaque, mature plaque, and/or both young and mature plaque. If the chosen plaque is selected to be young plaque, then the non-chosen plaque comprises mature plaque. Similarly, if the chosen plaque is selected to be mature plaque, then the non-chosen plaque comprises young plaque. Furthermore, if the chosen plaque comprises both young and mature plaque, then the non-chosen plaque is non-applicable. Moreover, the interfering species other than the chosen plaque can comprise dental hard tissue, dental filings, toothpaste, and any combination thereof. Other interfering species are also possible.

The light detector 74 is configured for detecting light ($\lambda_{site}$), identified by reference numeral 84, received from the evaluation site 80, wherein the detected light ($\lambda_{site}$) 84 comprises one or more of (i) a site reflected light ($\lambda_{refl}$) and (ii) a site emitted light ($\lambda_{em}$). Additional details regarding the light detector 74 will be provided herein below with reference to FIGS. 8 and 11-15.

The controller 76 operatively couples to the excitation source 72 and the light detector 74 via suitable signal lines, indicated via reference numeral 86. Controller 76 is configured for (i) controlling the excitation source 72 to output the wavelength modulated light and (ii) detecting plaque as a function of the detected light ($\lambda_{site}$) 84 and at least one higher harmonic of the wavelength modulation frequency higher than a fundamental. In one embodiment, controller 76 comprises one or more of a microprocessor, microcontroller, field programmable gate array (FPGA), integrated circuit, discrete analog or digital circuit components, hardware, software, firmware, or any combination thereof, for performing various functions as discussed herein, further according to the requirements of a given plaque detection implementation and/or plaque detection application. Controller 76 can further comprise one or more of the various modules, e.g., excitation control module, harmonic component detection module and others, as discussed herein.

Additional details regarding the controller 76 will be provided herein below with reference to FIGS. 8 and 11-15.

With reference still to FIG. 7, the plaque detection device 70 can further comprise an excitation control module 88, a harmonic component detection module 90 operatively coupled to at least the controller 76, e.g., via signal lines 86. The plaque detection device 70 can still further comprise an optics module 92. In one embodiment, the optics module 92 includes at least one of optical filters, optical fibers, collecting optical elements, and focusing optical elements optically coupled in a path of at least one of (i) the wavelength modulated light ($\lambda_{ex}$) 78 from the excitation source 72 to the evaluation site 80 and (ii) the detected light ($\lambda_{site}$) 84 from the evaluation site 80 to the light detector 74. Additional detail regarding the excitation control module 88, the harmonic component detection module 90 and optics module 92 will be provided herein below with reference to FIGS. 8 and 11-15.

The plaque detection device 70 can still further comprise a memory 94, user interface 96, a power source or power supply 98, and a communications module 100, all operatively coupled to at least the controller 76 via signal lines 86. In one embodiment, memory 94 can comprise any suitable memory device, operatively coupled to at least the controller 76, for at least storing information thereto that is based on at least one or more detection signal, and further for at least subsequently retrieving the information there from. User interface 96 can comprise any suitable user interface, operatively coupled to at least the controller 76, wherein responsive to a detected plaque detection signal, the user interface 96 at least outputs a user perceptible signal indicative of at least a status of detected presence of plaque at the evaluation site. For example, the user interface 96 can comprise at least one selected from the group consisting of: an input/output device, a tactile output device, a touch screen, a display device, an illumination output device, an audible output device, and any combination thereof.

The controller 76 outputs at least one signal as a function of detected plaque and indicative of a characteristic at the evaluation site that comprises at least one selected from the group consisting of (i) a presence of plaque, (ii) young plaque, (iii) mature plaque, and (iv) an absence of plaque. Accordingly, the user perceptible signal can comprise any suitable user perceptible signal selected according to the requirements of a given plaque detection implementation and/or plaque detection application, wherein the user perceptible signal is indicative of a characteristic at the evaluation site that comprises at least one selected from the group consisting of (i) a presence of plaque, (ii) young plaque, (iii) mature plaque, and (iv) an absence of plaque.

The power source 98 can comprise any suitable power source or power supply for a given plaque detection implementation and/or application. For example, for an oral healthcare appliance comprising an electric toothbrush, the power source 98 can comprise a rechargeable power source. The power source 98 could also comprise a power supply via a source external to the plaque detection device 70 or from a non-rechargeable power source.

The communication module 100 operatively couples to at least the controller 76, wherein responsive to the detection signal, the communication module 100 at least outputs a detection status signal to a remote device (102,104), wherein the detection status signal is indicative of at least a detection status of the presence of plaque at the evaluation site. The detection status signal may be further indicative of a characteristic at the evaluation site that comprises at least one selected from the group consisting of (i) a presence of plaque, (ii) young plaque, (iii) mature plaque, and (iv) an absence of plaque. In one embodiment, the remote device (102,104) comprises at least one selected from the group consisting of a mobile phone (not shown), a smart phone 102, a wired network enabled device (not shown) communicating via a network 104, a wire-less network enabled device (not shown) communicating via network 104, and any combination thereof.

Figure 8:
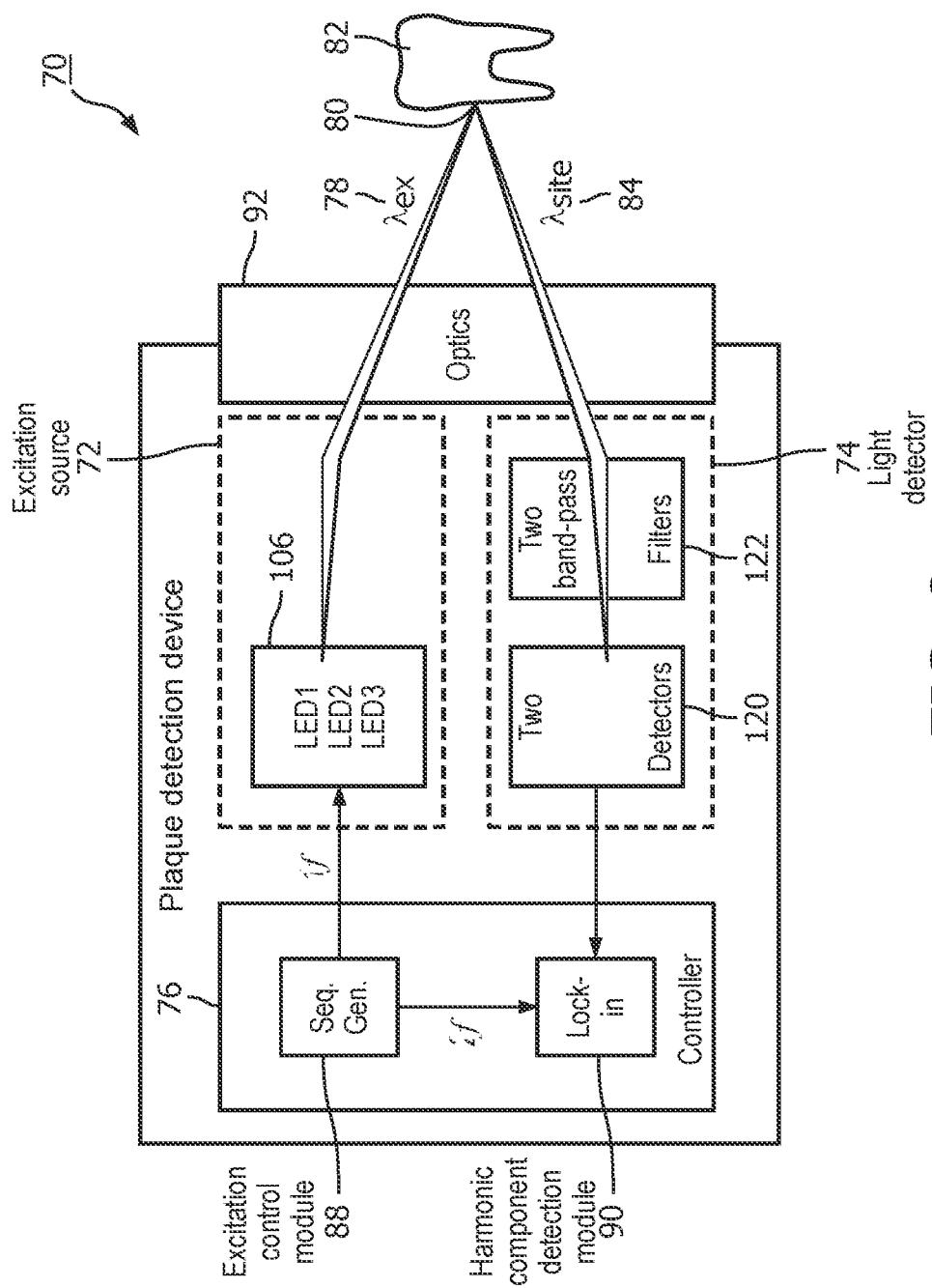
FIG. 8 is a block diagram view of a plaque detection apparatus that includes an excitation source having three LEDs, for detecting plaque using evaluation site emitted and/or reflected light, according to one embodiment of the present disclosure.

With reference now to FIG. 8, a block diagram view of a plaque detection apparatus 70 that includes an excitation source 72 having three LEDs 106, for detecting plaque using evaluation site emitted and/or reflected light, according to one embodiment of the present disclosure is shown. The three LEDs 106 are activated in a sequence 108 as a function of time, shown in FIG. 9. For example, with reference now to FIG. 9, during a first period 110, the activation sequence is as follows: LED1 OFF, LED2 ON, LED3 OFF (as indicated at reference numeral 112), LED1 ON, LED2 OFF, LED3 OFF (as indicated at reference numeral 114), LED1 OFF, LED2 ON, LED3 OFF (as indicated at reference numeral 116), and LED1 OFF, LED2 OFF, LED3 ON (as indicated at reference numeral 118). The sequence of the first period 110 has a duration of T=1/1f, where 1f is the fundament frequency.

Figure 9:
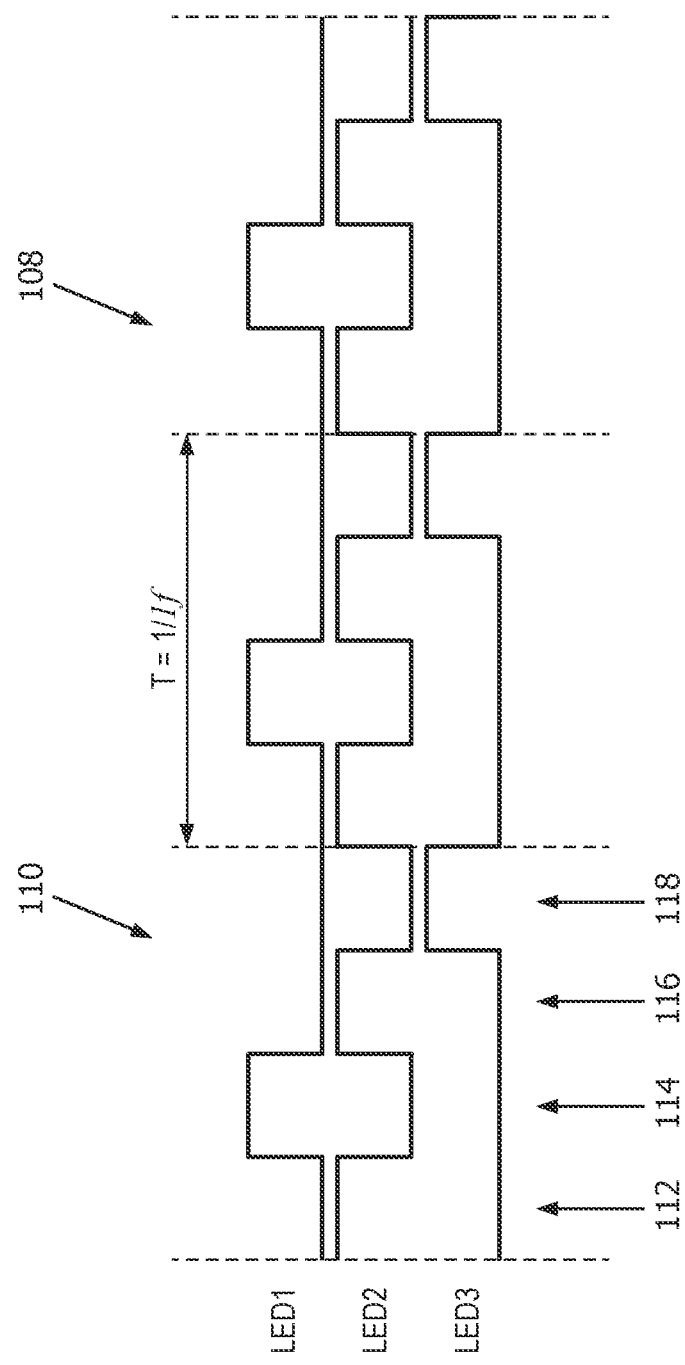
FIG. 9 is an illustrative timing diagram view of an excitation sequence for the three LEDs of the excitation source of FIG. 8, according to one embodiment of the present disclosure.

In one embodiment, the output of the excitation source 72 has a periodically changing wavelength, wherein the wavelength changes over a certain range centered around a central wavelength. The central wavelength aligns with the non-linearity in the spectrum, as discussed herein above. The frequency at which the wavelength is periodically changed, i.e., the wavelength modulation frequency, has a value of 1 f. Accordingly, 1 f is the frequency at which the sequence 108 of FIG. 9 is repeated.

For example, the light output of periodically changing wavelength includes wavelengths that comprise (i) a central wavelength that aligns with the non-linearity in the one or more of the absorption and fluorescence excitation spectrum for the chosen plaque (e.g., at the wavelength of light output from LED2), (ii) a wavelength shorter than the central wavelength (e.g., at the wavelength of light output from LED1), and (iii) a wavelength longer than the central wavelength (e.g., at the wavelength of light output from LED3). In one example, let's assume that the non-linearity is located at 444 nm. The wavelength of 444 nm is that of blue light, and the frequency of blue light is $6.67 \times 10^{14}$ Hz, wherein the frequency of blue light is not relevant in the context of the embodiments of the present disclosure. In this example, it is the wavelength of 444 nm (i.e., color) that is modulated—first the color is made more violet, then blue again, more cyan and finally blue again. Let's assume that the color (i.e., wavelength) cycle is repeated 1000 times per second (i.e., 1 kHz). The wavelength modulation frequency is thus 1 kHz. The second harmonic (e.g., the signal indicating young plaque) would then be 2 kHz.

Referring back to FIG. 8, in one embodiment, the light detector 74 comprises two photodiodes 120 and amplifiers and can also comprise collection and focusing optics like lenses, CPC's (Compound parabolic concentrator) or both. The light detector 74 further comprises two band pass filters 122, wherein the two band pass filters separate the two fluorescence bands (red and green) of both types of plaque (i.e., young and mature plaque) and reject the excitation light 78 reflected from the evaluation site 80.

Further with respect to the embodiment of FIG. 8, controller 76 can further comprise the excitation control module 88 and the harmonic component detection module 90. The excitation control module is configured for controlling, via at least one excitation control signal, the excitation source 72 to output the wavelength modulated light 78. The harmonic component detection module 90 is configured for detecting at least one harmonic component of the wavelength modulation frequency higher than a fundamental component contained within at least one of (i) an absorption spectrum that comprises site reflected light ($\lambda_{refl}$) and (ii) an excitation spectrum that comprises fluorescence emission in site emitted light ($\lambda_{em}$). In one embodiment, the harmonic component detection module 90 comprises at least one lock-in amplifier configured to detect the at least one higher harmonic component of the wavelength modulation frequency and to reject signals modulated at other frequencies.

In one embodiment, the harmonic component detection module 90 comprises at least one lock-in amplifier, the lock-in amplifier being configured to detect the second harmonic (2f) and to reject the tooth fluorescence which is modulated at the fundamental (1f). In another embodiment, the harmonic component detection module includes a synchronous rectifier followed by a low-pass filter. In yet another embodiment, the harmonic component detection module comprises a high-Q band pass filter.

Referring still to FIG. 8, the evaluation site 80 is separated from the plaque detection device 70 via a free space. In a further embodiment, instead of the free space as shown between the plaque detection device 70 and the evaluation site 80, the use of fiber optics or optical fibers, optically coupled between the detection device 70 and the evaluation site 80, is also possible.

As shown in FIG. 8, the excitation source 72 comprises three LEDs 106 for use in outputting three different wavelengths of light, the light detector 74 comprises at least one photodetector (e.g., two photodetectors can be used, one each for use in detecting one of two wavelength bands), and the excitation control module 88 includes a sequence generator for outputting the at least one excitation control signal configured for sequencing an excitation of the three LEDs 106 to produce a resultant light output 78 having the periodically changing wavelength centered around the wavelength corresponding to the non-linearity in the one or more of the absorption and the fluorescence excitation spectrum for the chosen plaque. In another embodiment, the three LEDs comprise blue LEDs that each output a narrow spectrum of light, and the three different narrow spectra of light comprise 438 nm, 444 nm and 450 nm.

Figure 10:
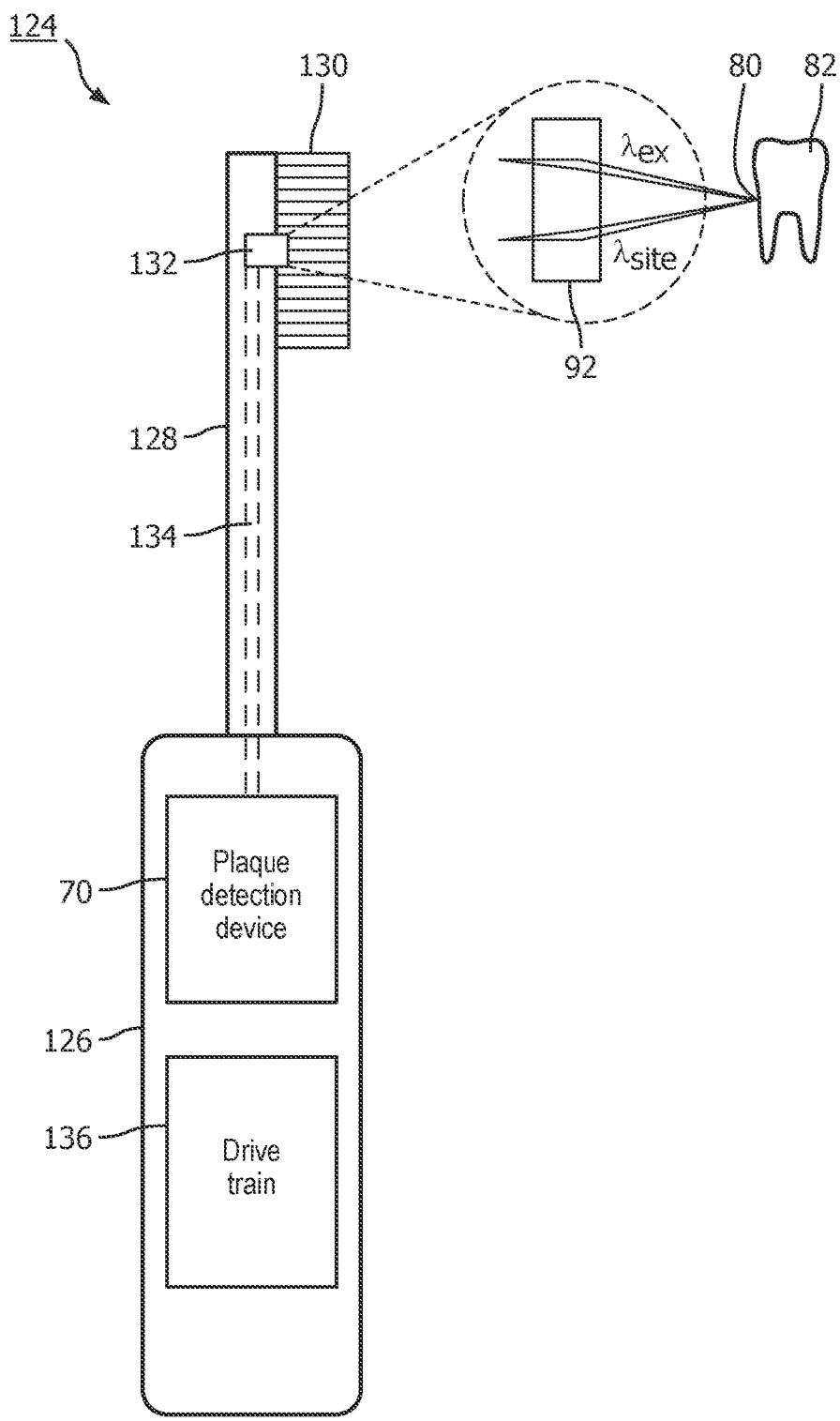
FIG. 10 is an illustrative block diagram view of an oral healthcare appliance including a plaque detection apparatus according to one embodiment of the present disclosure.

Referring now to FIG. 10, an illustrative block diagram view of an oral healthcare appliance 124 including a plaque detection apparatus 70 according to one embodiment of the present disclosure is shown. The oral healthcare appliance 124 includes a handle portion 126 for housing at least a first portion of the plaque detection apparatus 70. A distal end portion 128 extends from the handle portion 126 and is optically coupled via the optics module 92 with the plaque detection apparatus 70 for evaluating a site 80 for a presence of plaque via the distal end portion. The distal end portion 128 comprises at least one of (i) toothbrush bristles 130, and (iii) a probe 132 absent a presence of toothbrush bristles. In one embodiment, the optics module 92 includes at least one of optical filters, optical fibers, collecting optical elements, and focusing optical elements optically coupled in a path of at least one of (i) the wavelength modulated light ($\lambda_{ex}$) from the excitation source 72 to the evaluation site 80 and (ii) the detected light ($\lambda_{site}$) from the evaluation site 80 to the light detector 74. The distal end portion 128 can also include suitable optical fibers 134, wherein the optical fibers extend from the plaque detection device 70 to the probe 132 of the distal end portion 128. In one embodiment, oral healthcare appliance 124 comprises a power toothbrush, wherein the handle portion 126 houses a suitable drive train 136 for providing a desired driving energy to the distal end 128 for performing a brushing event, and to include detection of plaque via plaque detection device 70, according to one or more of the embodiments of the present disclosure.

Figure 11:
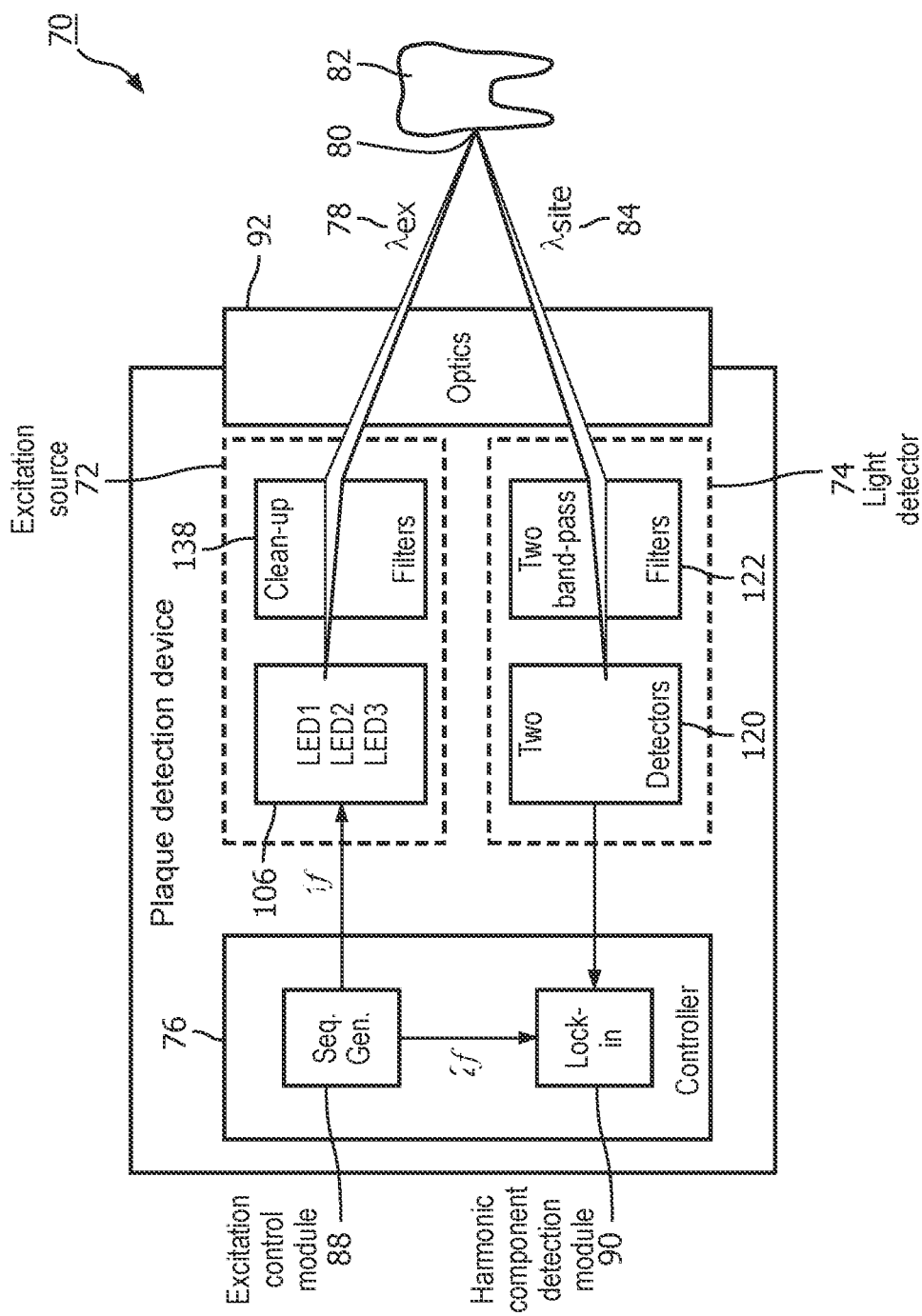
FIG. 11 is a block diagram view of a plaque detection apparatus that includes an excitation source having three LEDs, for detecting plaque using evaluation site emitted and/or reflected light, according to another embodiment of the present disclosure.

With reference now to FIG. 11, a block diagram view of a plaque detection apparatus 70 that includes an excitation source 72 having three LEDs 106, for detecting plaque using evaluation site emitted and/or reflected light, according to another embodiment of the present disclosure is shown. The embodiment of FIG. 11 is similar to that of FIG. 8, with the following differences. In this embodiment, the three LEDs 106 have an emission spectrum sufficient to cover a required range of the three different narrow spectra of light. The excitation source 72 further comprises three clean-up filters 138 arranged respectively at outputs of the three LEDs, one clean-up filter per LED. Each of the three clean-up filters 138 has a pass-band for a respective one of the three different narrow spectra of light.

Figure 12:
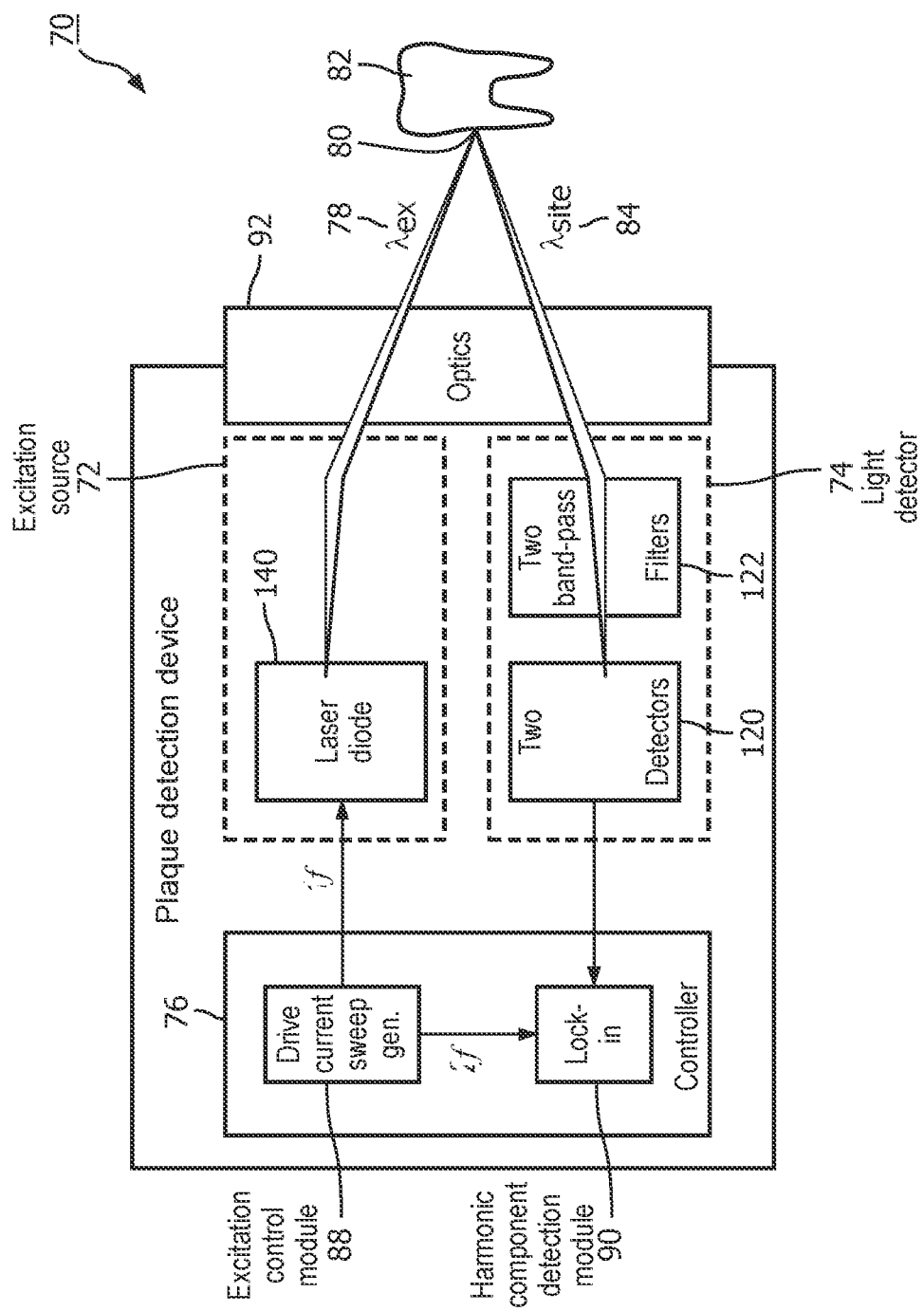
FIG. 12 is a block diagram view of a plaque detection apparatus that includes a laser diode excitation source, for detecting plaque using evaluation site emitted and/or reflected light, according to one embodiment of the present disclosure.

Turning now to FIG. 12, a block diagram view of a plaque detection apparatus 70 that includes a laser diode excitation source 72, for detecting plaque using evaluation site emitted and/or reflected light, according to one embodiment of the present disclosure is illustrated. The embodiment of FIG. 12 is similar to that of FIG. 8, with the following differences. In this embodiment, the excitation source 72 comprises a laser diode 140. In addition, the excitation control module 88 outputs the at least one excitation control signal configured for exciting the laser diode 140 to produce a resultant light output having the periodically changing wavelength centered around the wavelength corresponding to the non-linearity in the one or more of the absorption and the fluorescence excitation spectrum for the chosen plaque. For example, the excitation control module 88 can comprise a suitable drive current generator.

As illustrated, the embodiment of FIG. 12 uses a single light source: It is well known that the emission of a diode laser shifts with drive current. This behavior can be exploited to generate a wavelength sweep over the emission peak of young plaque. In addition, the detection path should be configured to compensate for intensity variations of the laser diode output. Such intensity variation compensation can be done by a time dependent gain compensation of the lock-in amplifier or photodiode amplifier. In other words, the gain compensation is locked to the drive current of the laser diode.

Figure 13:
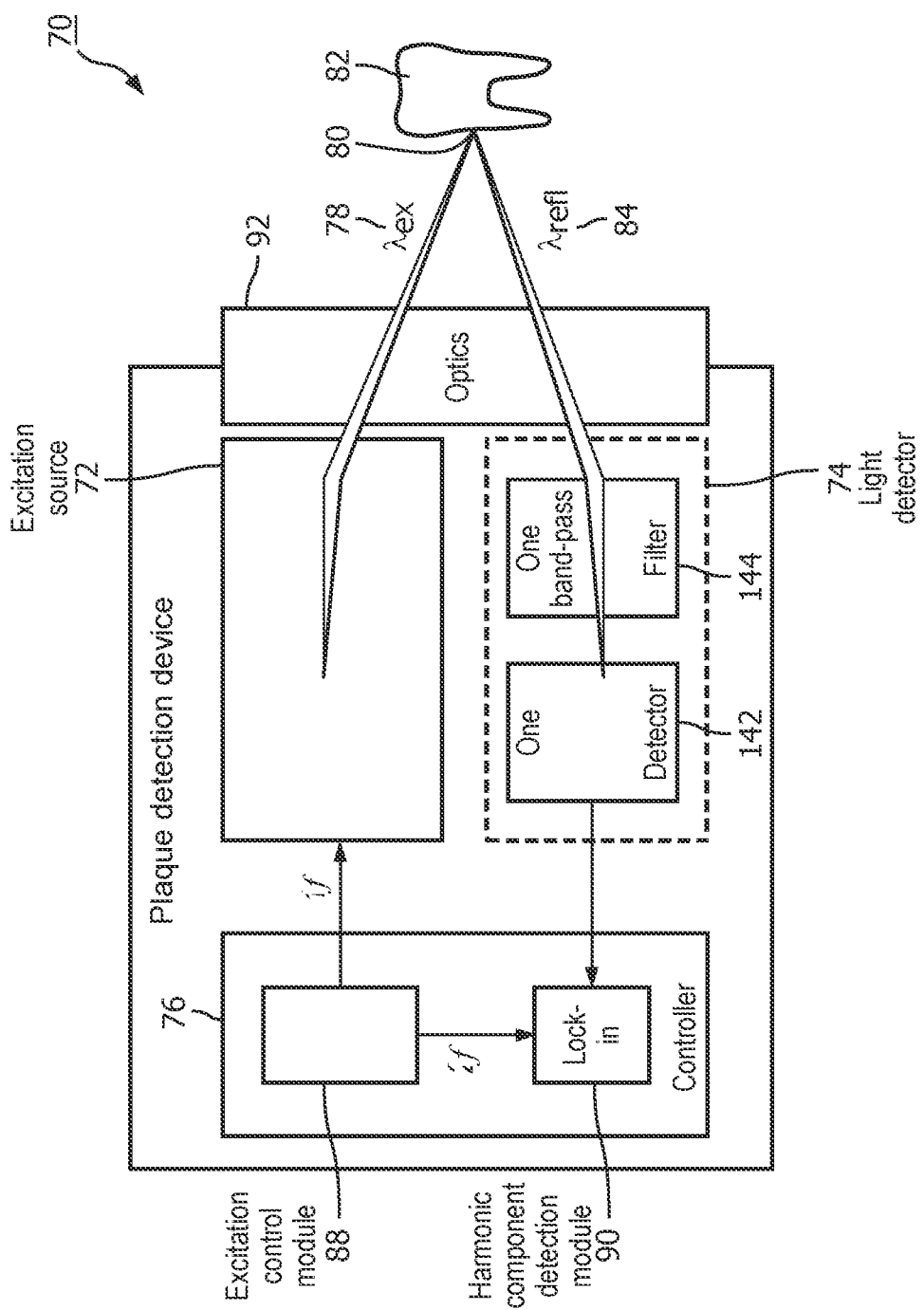
FIG. 13 is a block diagram view of a plaque detection apparatus that includes a controller and light detector, for detecting plaque using evaluation site reflected light alone, according to one embodiment of the present disclosure.

Turning now to FIG. 13, a block diagram view of a plaque detection apparatus 70 that includes a controller 76 and light detector 74, for detecting plaque using evaluation site reflected light alone, according to one embodiment of the present disclosure is shown. The embodiment of FIG. 13 is similar to the other embodiments of FIGS. 8, 11, 12, 14 and 15, with the following differences. In this embodiment, the light detector 74 comprises a photodetector 142 for use in detecting site reflected light, and one bandpass filter 144, wherein the bandpass filter has a pass-band for separating out a desired band of the site reflected light centered around the wavelength corresponding to the non-linearity in the absorption spectrum for the chosen plaque, while rejecting other bands of site reflected light.

One observation regarding the embodiment of FIG. 13 is that the embodiment is not based on fluorescence, but is based upon detection of the evaluation site reflected light. The detection branch comprises one band-pass filter (i.e., centered on the absorption peak) and one detector. Young plaque is detected using the second harmonic 2f, and mature or old plaque is detected using the third harmonic 3f.

With reference now to FIG. 14, a block diagram view of a plaque detection apparatus 70 that includes an excitation source 72 having a wide emission spectrum source 146 and tunable filter 148, for detecting plaque using evaluation site emitted and/or reflected light, according to an embodiment of the present disclosure is shown. The embodiment of FIG. 14 is similar to the other embodiments of FIGS. 8, 11, 12, 13 and 15, with the following differences. In this embodiment, the excitation source 72 comprises a wide emission spectrum fixed wavelength light source 146 and a tunable filter 148 arranged at an output of the wide emission spectrum fixed wavelength source, wherein tunable filter is operable for modulating a pass-band of the tunable filter among different wavelengths. The fixed wavelength source 146 provides an appropriate wide emission spectrum. The tunable filter (or modulated filter) 148 can comprise, for example, a tunable Fabry-Perot filter or a liquid crystal tunable filter. The excitation control module 88 outputs the at least one excitation control signal configured for tuning the tunable filter 148 to produce a resultant light output having the periodically changing wavelength centered around the wavelength corresponding to the non-linearity in the one or more of the absorption and the fluorescence excitation spectrum for the chosen plaque. For example, the excitation control module 88 can comprise a suitable filter tuning circuit and/or module.

Turning now to FIG. 15, a block diagram view is shown of a plaque detection apparatus 70 that includes an excitation source 72 having a wavelength tunable source 150, for detecting plaque using evaluation site emitted and/or reflected light, according to an embodiment of the present disclosure. The embodiment of FIG. 15 is similar to the other embodiments of FIGS. 8, 11, 12, 13 and 14, with the following differences. In this embodiment, the excitation source 72 comprises a wavelength tunable light source 150, wherein wavelength tunable light source is operable for being modulated among different wavelengths. The wavelength tunable source could comprise, for example, a light-emitting device with tunable color from ZnO nanorods, or the like. In addition, the excitation control module 88 outputs the at least one excitation control signal configured for tuning the wavelength tunable light source 150 to produce a resultant light output having the periodically changing wavelength centered around the wavelength corresponding to the non-linearity in the one or more of the absorption and the fluorescence excitation spectrum for the chosen plaque. For example, the excitation control module 88 can comprise a suitable wavelength tuning circuit and/or module.

In yet another embodiment, a plaque detection method, comprises providing wavelength modulated light ($\lambda_{ex}$) to an evaluation site. The wavelength modulated light is modulated at a wavelength modulation frequency to have a periodically changing wavelength centered around a wavelength corresponding to a non-linearity in one or more of an absorption and a fluorescence excitation spectrum for a chosen plaque, wherein the chosen plaque exhibits spectral characteristics different from spectral characteristics of one or more of (i) other plaque and (ii) interfering species other than the chosen plaque. Light ($\lambda_{site}$) received from the evaluation site is detected, wherein the detected light ($\lambda_{site}$) comprises one or more of (i) a site reflected light ($\lambda_{refl}$) and (ii) a site emitted light ($\lambda_{em}$). The method further comprises detecting plaque as a function of the detected light ($\lambda_{site}$) and at least one higher harmonic component of the wavelength modulation frequency higher than a fundamental.

While the embodiments of the present disclosure have been described mostly with reference to the second harmonic, the use of other harmonics is contemplated. In some instances, use of the second harmonic alone is sufficient. However, an assumption is made that the non-linearity has an even shape. The even shape of the spectrum will result in even harmonics including the second. As discussed herein, the second harmonic will have the highest amplitude and therefore the best to detect. Note however, that the 444 nm non-linearity for young plaque is not purely even, and thus, it will also introduce other harmonics. In addition, the central frequency may not be located exactly on the top of the non-linearity, which will also influence a distribution of the harmonics. In any event, one harmonic is sufficient for plaque detection, and additional harmonics can further provide more robust plaque detection. The use of digital signal processing, implemented via the controller, allows for detecting more frequencies concurrently, and therefore enables obtaining a greater specificity in the plaque detection.

Although only a few exemplary embodiments have been described in detail above, those skilled in the art will readily appreciate that many modifications are possible in the exemplary embodiments without materially departing from the novel teachings and advantages of the embodiments of the present disclosure. For example, the embodiments can be advantageously used in power toothbrush and/or other oral healthcare applications, including professional and/or specialized settings. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware, including analog and/or digital implementations, comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:
1. A plaque detection apparatus, comprising:
an excitation source comprising three LEDs for use in outputting three different narrow spectra of light configured to output wavelength modulated light to an evaluation site, the wavelength modulated light being modulated at a wavelength modulation frequency to have a periodically changing wavelength centered around a wavelength corresponding to a non-linearity in one or more of an absorption and a fluorescence excitation spectrum for a particular plaque, wherein the particular plaque exhibits spectral characteristics different from spectral characteristics of one or more of (i)

plaque other than the particular plaque and (ii) interfering species other than the particular plaque;

a light detector comprising at least one photodetector configured for detecting light received from the evaluation site, wherein the detected light comprises one or more of (i) a site reflected light and (ii) a site emitted light; and a controller comprising an excitation control module including a sequence generator for outputting at least one excitation control signal configured for sequencing an excitation of the three LEDs to produce a resultant light output having the periodically changing wavelength centered around the wavelength corresponding to the non-linearity in the one or more of the absorption and the fluorescence excitation spectrum for the particular plaque, operatively coupled to the excitation source and the light detector, and configured to (i) control the excitation source via the at least one excitation control signal, to output the wavelength modulated light and (ii) detect a presence of plaque based on the detected light and at least one higher harmonic of the wavelength modulation frequency higher than a fundamental;

the controller further comprising a harmonic component detection module for detecting at least one harmonic component of the wavelength modulation frequency higher than a fundamental component contained within at least one of (i) an absorption spectrum that comprises site reflected light and (ii) an excitation spectrum that comprises fluorescence emission in site emitted light.

2. The apparatus of claim 1, further wherein the harmonic component detection module comprises at least one lock-in amplifier configured to detect the at least one higher harmonic component of the wavelength modulation frequency and to reject signals modulated at other frequencies.

3. The apparatus of claim 1,
wherein the three LEDs comprise blue LEDs that each output a narrow spectrum of light, and the three different narrow spectra of light comprise 438 nm, 444 nm and 450 nm.

4. The apparatus of claim 1,
further wherein the three LEDs have an emission spectrum sufficient to cover a required range of the three different narrow spectra of light, wherein the excitation source further comprises three clean-up filters arranged respectively at outputs of the three LEDs, one clean-up filter per LED, wherein each of the three clean-up filters has a pass-band for a respective one of the three different narrow spectra of light.

5. The apparatus of claim 1,
wherein the light detector further comprises one bandpass filter, wherein the bandpass filter has a pass-band for separating out a desired band of the site reflected light centered around the wavelength corresponding to the non-linearity in the absorption spectrum for the particular plaque, while rejecting other bands of site reflected light.

6. A plaque detection apparatus, comprising:
an excitation source comprising a wide emission spectrum fixed wavelength light source and a tunable filter arranged at an output of the wide emission spectrum fixed wavelength source, wherein tunable filter is operable for modulating a pass-band of the tunable filter among different wavelengths, the excitation source configured to output wavelength modulated light to an evaluation site, the wavelength modulated light being modulated at a wavelength modulation frequency to have a periodically changing wavelength centered around a wavelength corresponding to a non-linearity in one or more of an absorption and a fluorescence excitation spectrum for a particular plaque, wherein the particular plaque exhibits spectral characteristics different from spectral characteristics of one or more of (i) plaque other than the particular plaque and (ii) interfering species other than the particular plaque;

a light detector comprising at least one photodetector configured for detecting light received from the evaluation site, wherein the detected light comprises one or more of (i) a site reflected light and (ii) a site emitted light; and a controller comprising an excitation control module configured to output at least one excitation control signal, operatively coupled to the excitation source and the light detector, and configured to (i) control the excitation source via at least one excitation control signal configured for tuning the tunable filter to produce a resultant light output having the periodically changing wavelength centered around the wavelength corresponding to the non-linearity in the one or more of the absorption and the fluorescence excitation spectrum for the particular plaque, to output the wavelength modulated light and (ii) detect a presence of plaque based on the detected light and at least one higher harmonic of the wavelength modulation frequency higher than a fundamental;

the controller further comprising a harmonic component detection module for detecting at least one harmonic component of the wavelength modulation frequency higher than a fundamental component contained within at least one of (i) an absorption spectrum that comprises site reflected light and (ii) an excitation spectrum that comprises fluorescence emission in site emitted light.

7. A plaque detection apparatus, comprising:
an excitation source comprising a wavelength tunable light source, wherein the wavelength tunable light source is operable for being modulated among different wavelengths, the excitation source configured to output wavelength modulated light to an evaluation site, the wavelength modulated light being modulated at a wavelength modulation frequency to have a periodically changing wavelength centered around a wavelength corresponding to a non-linearity in one or more of an absorption and a fluorescence excitation spectrum for a particular plaque, wherein the particular plaque exhibits spectral characteristics different from spectral characteristics of one or more of (i) plaque other than the particular plaque and (ii) interfering species other than the particular plaque;

a light detector comprising at least one photodetector, configured for detecting light received from the evaluation site, wherein the detected light comprises one or more of (i) a site reflected light and (ii) a site emitted light; and a controller comprising an excitation control module configured to output at least one excitation control signal, operatively coupled to the excitation source and the light detector, and configured to (i) control the excitation source via at least one excitation control signal configured for tuning the wavelength tunable light source to produce a resultant light output having the periodically changing wavelength centered around the wavelength corresponding to the non-linearity in the one or more of the absorption and the fluorescence excitation spectrum for the particular plaque to output the wavelength modulated light and (ii) detect a presence of plaque based on the detected light and at least one higher harmonic of the wavelength modulation frequency higher than a fundamental;

the controller further comprising a harmonic component detection module for detecting at least one harmonic component of the wavelength modulation frequency higher than a fundamental component contained within at least one of (i) an absorption spectrum that comprises site reflected light and (ii) an excitation spectrum that comprises fluorescence emission in site emitted light.

* * * * *